(12) United States Patent
Yang et al.

(10) Patent No.: US 10,967,161 B2
(45) Date of Patent: Apr. 6, 2021

(54) MEDICAMENT DELIVERY DEVICE, APPARATUS AND ASSEMBLY

(71) Applicant: Zhejiang Tanzhen Biotechnology Co., Ltd, Jiaxing (CN)

(72) Inventors: Yu-Ming Yang, Jiaxing (CN); Yang Yang, Jiaxing (CN)

(73) Assignee: ZHEJIANG TANZHEN BIOTECHNOLOGY CO., LTD, Jiaxing (CN)

( * ) Notice: Subject to any disclaimer, the term of this patent is extended or adjusted under 35 U.S.C. 154(b) by 0 days.

(21) Appl. No.: 17/041,621

(22) PCT Filed: Jul. 30, 2019

(86) PCT No.: PCT/CN2019/098466
§ 371 (c)(1),
(2) Date: Sep. 25, 2020

(87) PCT Pub. No.: WO2020/024953
PCT Pub. Date: Feb. 6, 2020

(65) Prior Publication Data
US 2021/0023352 A1 Jan. 28, 2021

(30) Foreign Application Priority Data
Aug. 1, 2018 (CN) .......................... 201810867675.4

(51) Int. Cl.
*A61M 31/00* (2006.01)
*A61B 17/00* (2006.01)
(Continued)

(52) U.S. Cl.
CPC ....... *A61M 31/00* (2013.01); *A61B 17/00234* (2013.01); *A61M 39/10* (2013.01); *A61M 39/22* (2013.01); *A61M 2202/064* (2013.01)

(58) Field of Classification Search
CPC ...... A61B 17/00234; A61M 2202/064; A61M 31/00; A61M 39/10; A61M 39/22;
(Continued)

(56) References Cited

U.S. PATENT DOCUMENTS 4,306,705 A * 12/1981 Svensson ................. A61B 5/20
251/148
4,722,725 A * 2/1988 Sawyer .................... A61M 5/36
604/122
(Continued)

FOREIGN PATENT DOCUMENTS

CN 1733329 A 2/2006
CN 203971181 U 12/2014
(Continued)

*Primary Examiner* — Brandy S Lee
(74) *Attorney, Agent, or Firm* — WPAT, PC

(57) ABSTRACT

A device includes a container for accommodating a medicament, a pressure route and a valve. The pressure route, disposed in the container, includes an extending pathway, a pressure-route inlet connected with a connecting port, and a pressure-route outlet extending toward a container bottom. The valve includes a first through hole connecting spatially the pressure-route inlet and outlet, and a valve body dividing the extending pathway into a pressure-in pathway and a pressure-out pathway. The device can convey the medicament such as a hemostatic agent more stably and smoothly to effectively avoid blocking upon a field of vision of an endoscope by the disturbed medicament while hitting a target tissue. Thereupon, the medicament can be provided more precisely, continuity of an endoscopic surgery can be improved, efficiency of hemostasis can be enhanced, and also surgery time can be substantially shortened.

12 Claims, 5 Drawing Sheets

(51) Int. Cl.
*A61M 39/10* (2006.01)
*A61M 39/22* (2006.01)

(58) Field of Classification Search
CPC .............. A61M 1/0035; A61M 1/0043; A61M 1/0045; A61M 1/00
See application file for complete search history.

(56) References Cited

U.S. PATENT DOCUMENTS

| 4,958,751 A | 9/1990 | Curtis et al. |
| 2007/0240714 A1 | 10/2007 | Dunne et al. |
| 2016/0114112 A1* | 4/2016 | Riebman ............... B05B 12/124 604/500 |

FOREIGN PATENT DOCUMENTS

| CN | 203971182 U | 12/2014 |
| CN | 105194771 A | 12/2015 |
| CN | 107126616 A | 9/2017 |
| CN | 108938015 A | 12/2018 |
| CN | 109674495 A | 4/2019 |
| WO | WO201506240 A1 | 5/2015 |

* cited by examiner

MEDICAMENT DELIVERY DEVICE, APPARATUS AND ASSEMBLY

CROSS REFERENCE TO RELATED APPLICATION

This application claims the benefits of China application Serial No. 201810867675.4, filed on Aug. 1, 2018, the disclosures of which are incorporated by references herein in its entirety.

TECHNICAL FIELD

The present disclosure relates in general to a medicament delivery container, and more particularly to a device that is driven by a pressure source to deliver a medicament to a target tissue, and so the medicament can be easily to perform a desired treatment.

BACKGROUND

Currently, no matter what kind of hemostatic treatments is applied to a body bleeding caused either by a wound or by a surgery, a step of depression to hemostasis is always necessary. In the art, medical accessories for hemostasis include band aids for external trauma, hemostatic sponges, hemostatic micro spheres, medical hemostatic membranes, hemostatic yarns made by non-woven technology, and so on. Though efficiency of hemostatic treatments can be increased by applying these accessories, yet a depression step for a period of time before the wound can be applied further treatments is required. After this depression period, it should be confirmed if any bleeding at the would is still there. In the case that the bleeding is still true, a hemostatic agent may be applied to the wound, and then the depression step shall be resumed till a hemostatic state is achieved. Such a hemostatic operation is obviously tedious and human-dependent. To a hemostatic treatment upon a bleeding wound at an internal organ or duct, the aforesaid hemostatic operation is usually hard to be performed accurately. In other words, to this type of wounds, a satisfied hemostatic treatment is barely to be obtained. Generally, if bleeding of a wound can be stopped only through a long-term local depression, a future healing of this wound would be an issue to be concerned. By having the bleeding in nasal sinus or nasal cavity as an example, an expanded hemostatic sponge is usually used for hemostasis, but it is easy to see that a complete hemostatic operation is hard to achieved. Generally, a 24-hour depression for the hemostatic sponge to stay in the nasal sinus or nasal cavity shall be needed, before the hemostatic sponge can be removed. Sometimes, the patients with this hemostatic treatment may meet nasal swelling, respiratory tract obstruction, and hemostatic difficulty in a following surgery. To those weak patients, an additional 24-hour observation and a possible secondary hemostatic treatment might be necessary, and thus work load upon related medical staff would be increased.

Though introduction of a hemostatic gel may improve bleeding at the wound, yet it might be less helpful in treating a major bleeding wound in a shorter time. It is obvious that the application of the hemostatic gel has a shortcoming in timing hemostasis.

In the marketplace, a spraying product can be applied to transfer the medicament onto the wound. Such a spraying product for evenly distributing the medicament powder is actually a powder-spraying means, not a direct hemostasis device. For example, though the well-known Yun-Nan white medicinal powder spray mainly for muscle sprains can be used to treat bruises and cuts, yet, according to the instructions, some other hemostatic medicament or direct depression shall be still applied for promoting the hemostasis.

In China utility patent No. ZL201420372934.3, a hemostasis device for wound and an assembly thereof are disclosed to include a container for holding a hemostatic medicament, a valve connected with a foreign pressure source and used for controlling open/close of the container, an application tube having one bent end, and a Tee connector connecting spatially the container, the valve and the application tube. The device can perform rapid hemostasis upon a bleeding tissue. However, since a pressure overshoot exists at the moment of opening the valve to escalate the injection pressure for driving the medicament powder, the initial injection of the hemostatic medicament powder would impact the tissue, and part of the powder would be bounced back possibly to block the field of vision upon the wound. Thereupon, continuous observation would be unfeasible. By have a laparoscopic surgery for example, the bounced-back hemostatic medicament powder would contaminate the laparoscope, and thus a clear observation for the surgery would be impossible. In other words, with this device, hemostasis effect and real-time observation of the surgery would be adversely affected, and thus the success rate and persistence of the endoscopic surgery would be reduced.

SUMMARY

An object of the present disclosure is to provide a medicament delivery device that is driven by a pressure source to deliver a medicament to a target tissue, and so the medicament can be easily to perform a desired treatment.

Another object of this present disclosure is to provide a medicament delivery device that can provide a stable internal pressure to the medicament. Thereupon, the medicament can be prevented from being impacted by a drive fluid, but driven continuously and evenly to avoid possible impact damages at the target tissue.

A further object of this present disclosure is to provide a medicament delivery device that can provide a stable pressure to a hemostatic agent in the device. Thereupon, the hemostatic agent can be continuously and evenly propelled by the drive fluid to reach precisely the bleeding tissue for avoiding multi-hemostasis applications at the bleeding tissue, and thus an adequate amount of the hemostatic agent is required for the hemostatic treatment at the bleeding tissue.

One more object of this present disclosure is to provide a medicament delivery apparatus that a device thereof can be fixed with parts such as guide pipes, or integrated with the parts as a unique piece. Thereupon, the target tissue can be prevented from being impacted or irrelevantly forced by the medicament, and so vision of field can be clear, without be foggy, for endoscopic applications.

One further more object of this disclosure is to provide a medicament delivery assembly that a device thereof can be furnished with parts such as guide pipes. Thereupon, the target tissue can be prevented from being impacted or irrelevantly forced by the medicament, and so vision of field can be clear, without be foggy, for endoscopic applications.

A device, applied to deliver medicament, comprises:
a container for accommodating the medicament;
a pressure route, including an extending pathway, a pressure-route inlet and a pressure-route outlet, the pressure-route outlet extending toward a bottom of the container; and
a valve, including a first through hole and a valve body, the first through hole connecting spatially the pressure-route inlet and the pressure-route outlet, the valve body dividing the extending pathway into a pressure-in pathway and a pressure-out pathway.

In one embodiment of this disclosure, the device further includes a connecting port disposed at the container, and one end of the connecting port for introducing a fluid being connected with a pressure source.

In this disclosure, another device comprises:
a container for accommodating a medicament;
a connecting port, disposed at the container and used for connecting a pressure source;
a pressure route, extending inside the container, including an extending pathway, a pressure-route inlet and a pressure-route outlet, the pressure-route inlet being connected with the connecting port, the pressure-route outlet being disposed by facing a bottom of the container; and
a valve, including a first through hole and a valve body, the first through hole connecting spatially the pressure-route inlet and the pressure-route outlet, the valve body dividing the extending pathway into a pressure-in pathway and a pressure-out pathway.

In one embodiment of this disclosure, the device further includes a blocking member furnished with the first through hole and used for sealing the first through hole.

In one embodiment of this disclosure, the valve body further includes a guide member applied to have the pressure-out pathway and the pressure-in pathway to extend toward the first through hole.

In this disclosure, the valve body of the device is to change at least once the flow direction of the fluid along the pressure-out pathway. In some embodiments, the flow direction may be turned twice, three times, four times or more.

In one embodiment of this disclosure, the valve body further includes a first turning member disposed inside the pressure-out pathway to turn the flow direction of the fluid in the pressure-out pathway for the first time.

In one embodiment of this disclosure, the valve body further includes a second turning member disposed inside the pressure-out pathway to turn the flow direction of the fluid in the pressure-out pathway for the second time.

In one embodiment of this disclosure, after the valve body turns at least twice the flow direction of the fluid in the pressure-out pathway, the fluid in the pressure-out pathway would flow toward the pressure-route outlet.

In one embodiment of this disclosure, the pressure source is to provide a pressurized fluid such as a gas or a liquid, preferably a gas such as, but not limited to, air, $N_2$, $O_2$, $CO_2$ or an inert gas.

In one embodiment of this disclosure, another device further includes a medicament accommodated in the container, and the medicament is powdery and has more than 90% of powder particles with a grain size ≤100 μm; preferably ≤50 μm.

In this disclosure, the medicament enters the container via the pressure-route outlet, and leaves the container via a container outlet.

In order to apply the medicament directly onto a target tissue, a connection tube is further provided to the container outlet for engaging the medicament delivery device of this disclosure. Through the connection tube to guide the conveying path of the medicament, the medicament can be better discharged right at the target tissue or at a place adjacent to the target tissue.

In order to facilitate an endoscopic surgery, and to avoid adverse impact or reactive bounce back of the medicament upon the target tissue, from which the field of vision of the endoscope may be blocked by contaminating the medicament powder, this disclosure further provides a pressure-adjusting assembly to engage the medicament delivery device.

The pressure-adjusting assembly includes:
a pressure-adjusting tunnel has one open end connected with the connection tube, and another open end of the pressure-adjusting assembly has a tunnel wall forming an angle, ranging between 3°~10°, with an axial direction of the pressure-adjusting tunnel.

The medicament is discharged directly onto a target tissue via another open end of the connection tube.

In order to improve the pressure applied on the target tissue, another pressure-adjusting assembly of this disclosure includes:
a pressure-adjusting tunnel, having a tunnel inlet connected with the connection tube and a tunnel outlet further having a tunnel wall forming an angle with an axial direction of the pressure-adjusting tunnel, in which the angle is ranging between 10°~12.5°; and
an injection nozzle, having an injection-nozzle inlet engaged with the tunnel outlet and an injection-nozzle outlet further having a tunnel wall forming an angle with an axial direction of the injection nozzle, in which the angle is ranging between 5°~6°;
wherein, in a radial direction of the pressure-adjusting tunnel, the tunnel wall of the pressure-adjusting tunnel further includes a plurality of grooves.

The injection-nozzle inlet and the tunnel outlet have the same diameter, and a buffer segment is disposed between the injection-nozzle inlet and the injection-nozzle outlet. The buffer segment has an axial length of 0.5 mm~2 mm, preferably 0.5 mm~1.5 mm.

The medicament is discharged directly onto the target tissue from an open end of the pressure-adjusting assembly.

In this disclosure, various devices can be applied to pair the connection tube and the pressure-adjusting assembly by assembling, 3D printing or die casting. The device, the connection tube and the pressure-adjusting assembly can be manufactured as a unique piece for transferring the medicament. In applications, for these products to be all disposable medical supplies, manufacturing and use would be much easier.

Advantages of this Disclosure:

After connecting the pressure source, the device of this disclosure can provide more stable and more balanced forcing to convey accurately and smoothly the medicament inside the container to the bleeding tissue, such that bounce back effect of the medicament upon the target tissue can be prevented from blocking the field of vision of the endoscope or contaminating lens of the endoscope, definitely from which action of the medicament upon the target tissue (especially, the hemostatic action of the hemostatic agent upon the target tissue) cannot be clearly observed in a real-time manner.

After connecting the pressure source, the device of this disclosure can provide more stable and more balanced forcing to output more gently the medicament from the container, and so the continuity of the endoscopic surgery can be improved.

After engaging the pressure-adjusting assembly, the device of this disclosure can concentrate the distribution of the pressurized medicament over the target tissue, especially the bleeding tissue, so that the administration of the hemostatic medicament can be more accurate. For example, more than 75% of the medicament can be limited within an area having a radius between 0.5 cm~1.5 cm.

The device of this disclosure can concentrate the medicament propelled by the pressure source over the target tissue, especially the bleeding tissue, such that more medicament can be directly applied to the bleeding wound surface, and so the hemostasis time can be significantly shortened; for example, effective hemostasis within 20 seconds.

In comparison with the solutions provided by China Utility Patent No. ZL201420372934.3, the device provided by this disclosure can convey the hemostatic medicament powder directly and accurately to the bleeding tissue, such that the bounce back effect of the hemostatic medicament powder can be avoided. Thereupon, possible powder contamination to make vague the field of vision of the endoscope would be inhibited, and thus the endoscopic surgery can be normally operated. Also, since the hemostatic treatment can be directly and accurately performed on the bleeding tissue, the total time for the endoscopic surgery can be greatly reduced.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
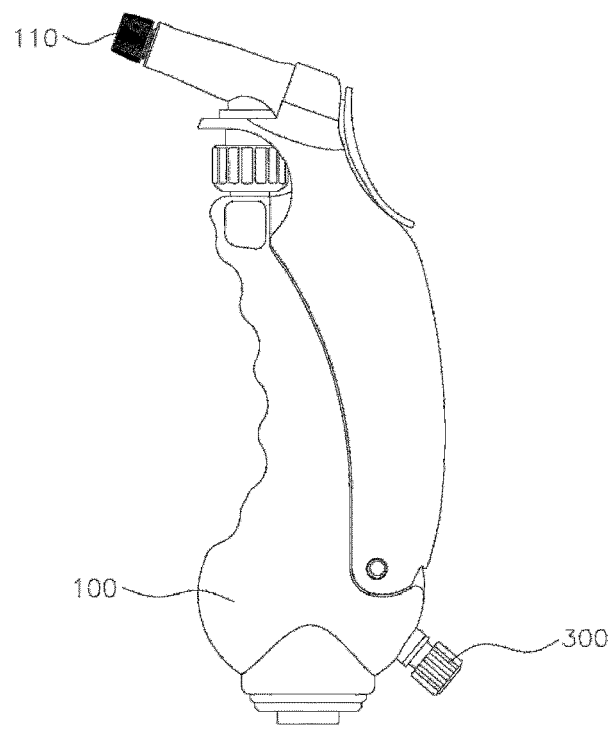
FIG. 1 is a schematic view of an embodiment of a device in accordance with this disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
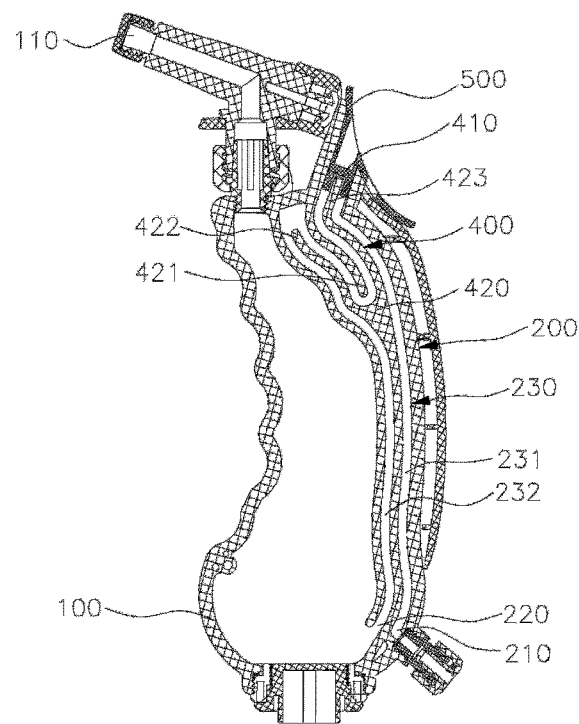
FIG. 2 is a schematic cross-sectional view of FIG. 1.

Refer now to FIG. 1 and FIG. 2; where FIG. 1 is a schematic view of an embodiment of a device in accordance with this disclosure, and FIG. 2 is a schematic cross-sectional view of FIG. 1. As shown, in this embodiment, the device includes a container 100 and a pressure route 200. A connecting port 300, furnished to the container 100, is used for connecting a pressure source. In this embodiment, the pressure source provides an expected pressurized fluid, either a gas or a liquid, preferably a gas such as, but not limited to, air, $N_2$, $O_2$, $CO_2$ or an inert gas. The connecting port 300 is further connected with the pressure route 200 so as to introduce the pressurized fluid into the pressure route 200.

The pressure route 200, furnished inside the container 100, includes an extending pathway 230, a pressure-route inlet 210 and a pressure-route outlet 220. The pressure-route inlet 210 is connected with the connecting port 300, and the pressure-route outlet 220 is disposed to face a bottom of the container 100. The pressurized fluid is introduced into the extending pathway 230 via the pressure-route inlet 210, so as to flow along the extending pathway 230. The pressurized fluid leaves the extending pathway 230 via the pressure-route outlet 220, and then meets the medicament inside the container 100. The medicament, then driven by the pressurized fluid, is conveyed therewith and toward a container outlet 110.

After a pressure-source valve is opened, the fluid from the pressure source would enter the pressure route 200, and then flow quickly to leave the pressure route 200 via the pressure-route outlet 220, such that the medicament close to the pressure-route outlet 220 would be suddenly driven to move toward the container outlet 110.

Figure 7:
FIG. 7 is a schematic view of a medicament distribution on a target tissue by a conventional design.

After the medicament with a larger momentum hits a target tissue, a reaction from the target tissue would broaden an area to accept the medicament as shown in FIG. 7. Accordingly, the medicament is dispersedly distributed, and thus the concentration of the medicament on the target tissue is reduced as well. Hence, while in an endoscopic surgery, with the reaction from the target tissue, the medicament would scatter all over the field of vision, by which a normal endoscopic surgery would be hard to proceed. Thus, it is inevitable to suspend the surgery, and to retrieve the endoscope for cleaning. Thereupon, continuity and efficiency of the endoscopic surgery would be affected.

In order to avoid the aforesaid situation, the device of this disclosure further includes a valve 400, and the valve 400 includes a first connecting channel 410 and a valve body 420. The first connecting channel 410, open to the atmosphere, is connected individually and spatially far to the pressure-route inlet 210 and the pressure-route outlet 220. The valve body 420, disposed inside the pressure route 200, would separate the extending pathway 230 into a pressure-in pathway 231 and a pressure-out pathway 232.

After the pressure-source valve is opened, the fluid from the pressure source would pass through the pressure-route inlet 210 and then enter the pressure route 200 to flow along the pressure-in pathway 231 before entering the first connecting channel 410. Upon when the fluid flow from the pressure source is stable, an optional blocking member 500 applied to plug the first connecting channel 410 can allow the fluid from the pressure source to enter the pressure-out pathway 232 and then to leave via the pressure-route outlet 220 to meet the medicament at the bottom of the container 100. According to this disclosure, the fluid from the pressure source can be present to drive the medicament in a more stable manner by controlling the blocking member 500 to plug or open the first connecting channel 410. In the case that the first connecting channel 410 is plugged, then the pressured fluid would flow from the pressure-in pathway 231 to the pressure-out pathway 232. On the other hand, in the case that the first connecting channel 410 is open, then the pressured fluid from the pressure-in pathway 231 would be directly discharged into the atmosphere. Since forcing upon the medicament can be more evenly, thus, when the medicament hits the target tissue, the reaction from the target tissue would be reduced, and the medicament would be more concentrated on the target tissue.

To an endoscopic surgery, the device reduces the reaction of the target tissue against the medicament, so that the medicament would not be severely bounced back to contaminate the endoscope by partly blocking the field of vision, and such that the surgery can be continuously executed. Timing for plugging the first connecting channel 410 can be determined according to practical situations. For example, in a surgery, a user can use his/her thumb to depress the blocking member 500 to plug the first connecting channel 410. While the first connecting channel 410 is plugged, the fluid from the pressure source would be led into the pressure-out pathway 232, and then leave the pressure route 200 via the pressure-route outlet 220. Obviously, the operation of the device is much easier that the prior art. For another example, in a product package, with the blocking member 500 to plug the first connecting channel 410, insides of the device can be kept sterile during transportation and storage.

In order to control the flow rate of the fluid from the pressure source, a flowmeter can be used for monitoring and facilitating the adjustment of the flow rate.

In order to prevent the fluid from the pressure source in an initial stage of entering the extending pathway 230 from hitting the medicament with an overshoot momentum, the valve body 420 can further include a guide member 423 for guiding the pressure-in pathway 231 and the pressure-out pathway 232 to extend toward the first connecting channel 410.

Empirically, by changing a flow direction of the fluid from the pressure source, the aforesaid problem in overshoot momentum upon the medicament at the early stage while the fluid entering the extending pathway 230 can be substantially resolved so as to have the forcing upon the medicament in a more stable and smoother manner. In the device of this disclosure, a commutator can be furnished to the valve body 420 so as to turn the flow direction of the fluid in the pressure-out pathway 232 at least once by 90°~180°. In some other embodiments, the flow direction can be turned twice, three times, four times or more times.

In this embodiment, the valve body 420 further includes a first turning member 421 disposed in the pressure-out pathway 232 for making the first 180° turn of the fluid in the pressure-out pathway 232. In addition, a second turning member 422 can be also included in the pressure-out pathway 232, such that the pressure-out pathway 232 can make its second 180° turn before flowing toward the pressure-route outlet 220. In the case that the grain size of the medicament is too small, more commutators can be applied to change the flow direction of the fluid, such that the forcing upon the medicament by the fluid can be much gentle. Thereupon, the aforesaid problems in overshoot momentum, excessive reaction from the target tissue, broader medicament action area (as shown in FIG. 7), disperse medicament distribution, and less medicament concentration on the target tissue.

In this disclosure, the medicament for the target tissue is powdery with more than 90% of the particles having a grain size ≤100 µm, preferably ≤50 µm. The fluid discharged from the pressure-route outlet 220 would push the medicament to move toward the container outlet 110 so as to allow the medicament to coat the target tissue.

In order to have the medicament to be directly applied to the target tissue, a connection tube 600 can be furnished to the container outlet 110 of the device. The connection tube 600 is used for guiding the medicament leaving the container outlet 110, so that the medicament can be discharged in a position close to the target tissue.

In order to help the endoscopic surgery, to avoid possible impact at the target tissue by the medicament, and to lessen the contamination of the endoscope by the bounce-back medicament, this disclosure further provides a pressure-adjusting assembly 700 to cooperate the device and the connection tube 600.

Figure 3:
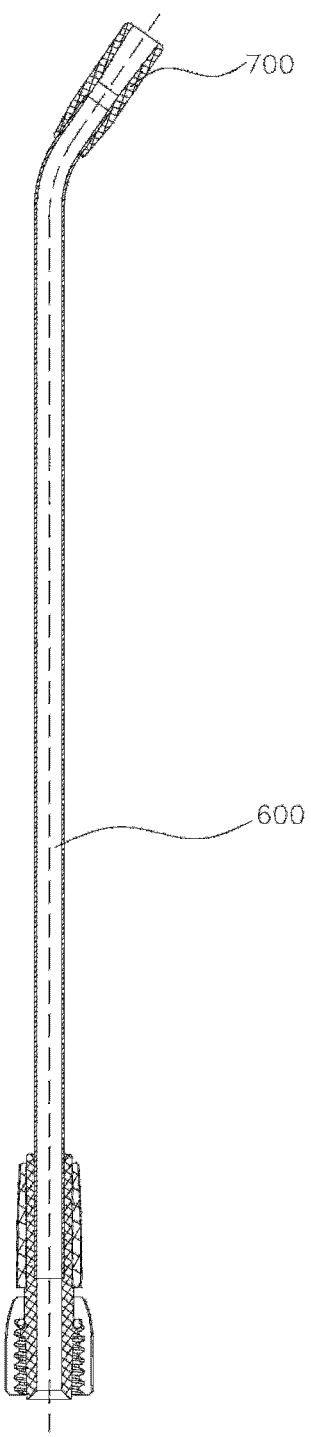
FIG. 3 is a schematic cross-sectional view of an embodiment of the connection tube furnished with a pressure-adjusting assembly in accordance with this disclosure.
Figure 5:
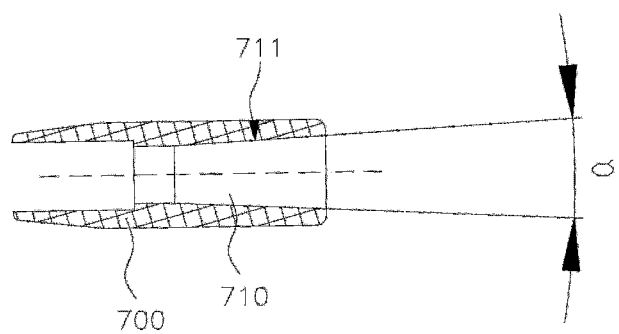
FIG. 5 is a schematic cross-sectional view of an embodiment of the pressure-adjusting assembly in accordance with this disclosure.
Figure 8:
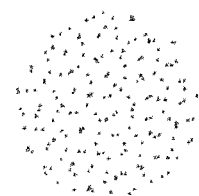
FIG. 8 is a schematic view of a medicament distribution on a target tissue by the apparatus of this disclosure.

FIG. 3 is a schematic cross-sectional view of an embodiment of the connection tube furnished with a pressure-adjusting assembly 700 in accordance with this disclosure, and FIG. 5 is a schematic cross-sectional view of an embodiment of the pressure-adjusting assembly in accordance with this disclosure. As shown, in this embodiment, the pressure-adjusting assembly 700 includes a pressure-adjusting tunnel 710 having an open end connected with the connection tube 600 and another open end having a tunnel wall 711 forming an axial angle with the pressure-adjusting tunnel by 3°~10°. The medicament guided by the connection tube 600 would be discharged via the pen end having the 3°~10° axial angle, and then applied onto the target tissue by forming an action area shown in FIG. 8.

Figure 6:
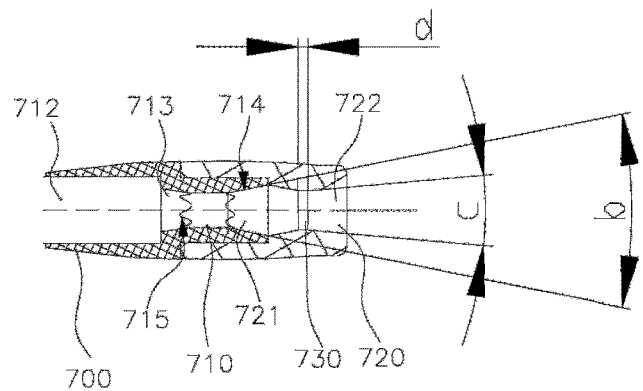
FIG. 6 is a schematic cross-sectional view of another embodiment of the pressure-adjusting assembly in accordance with this disclosure.

FIG. 6 is a schematic cross-sectional view of another embodiment of the pressure-adjusting assembly in accordance with this disclosure. As shown, the pressure-adjusting assembly 700 includes a pressure-adjusting tunnel 710 having a tunnel inlet 712 connected with the connection tube 600 and an opposing tunnel outlet 713 having a tunnel wall 714 forming an axial angle b with the pressure-adjusting tunnel 710 by 10°~12.5°. In addition, along a radial direction of the pressure-adjusting tunnel 710, a plurality of grooves 715 is furnished to the tunnel wall of the pressure-adjusting tunnel 710.

Figure 9:
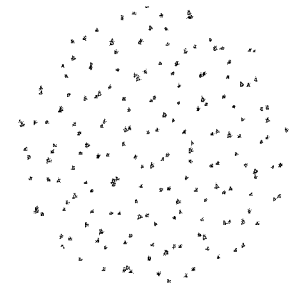
FIG. 9 is a schematic view of another medicament distribution on a target tissue by the apparatus of this disclosure.

Also, an injection nozzle 720 is furnished to a front portion of the pressure-adjusting tunnel 710. The injection nozzle 720 has an injection-nozzle inlet 721 connected with the tunnel outlet 713 and an injection-nozzle outlet 722 having a tunnel wall forming an axial angle c with the injection nozzle 720 by 5°~6°. With the connection tube 600 to discharge the medicament from the open end having the axial angle, the medicament can be directly applied to the target tissue by forming a medicament action area on the target tissue, as shown in FIG. 9.

In this embodiment, the injection-nozzle inlet 721 and the tunnel outlet 713 have the same diameter. Between the injection-nozzle inlet 721 and the injection-nozzle outlet 713, a buffer segment 730 is formed by having an axial length d of 0.5 mm~2 mm, preferably 0.5 mm~1.5 mm.

Figure 4:
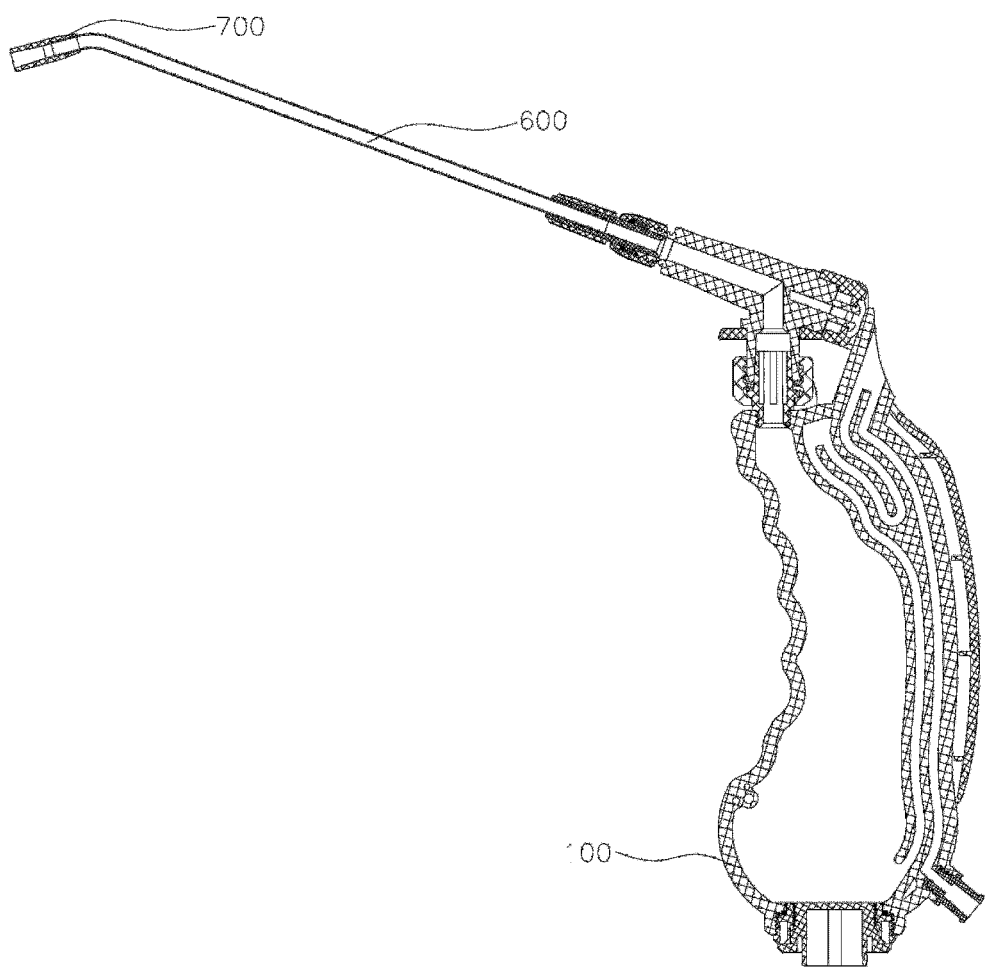
FIG. 4 is a schematic cross-sectional view of an embodiment of the apparatus in accordance with this disclosure.

FIG. 4 is a schematic cross-sectional view of an embodiment of the apparatus in accordance with this disclosure. Referring to FIG. 1 and FIG. 4, the apparatus of this disclosure is further furnished with a pressure-adjusting assembly 700 disposed at one end of the connection tube 600, while another end of the connection tube 600 is connected with the device. With the hemostatic medicament (see ZL2015100443818) loaded to the apparatus of this disclosure for performing hemostasis treatment upon a bleeding tissue, the connecting port 300 and the air source are connected to introduce a pressurized fluid. Then, the connection tube 600 is moved to aim at the bleeding target tissue, and then the blocking member 500 at the first connecting channel 410 is depressed so as to allow the pressurized fluid to enter the pressure-out pathway 232. After two 180° turns, the fluid would move toward the pressure-route outlet 220, and meet the medicament after being discharged into the container 100 via the pressure-route outlet 220. With the flow of the fluid, the medicament at the bottom of the container 100 would be driven to be discharged via the free open end of the connection tube, and then applied to the bleeding wound surface. By adjusting the flow rate of the fluid, the hemostasis process at the target tissue can be preferably observed.

Figure 10:
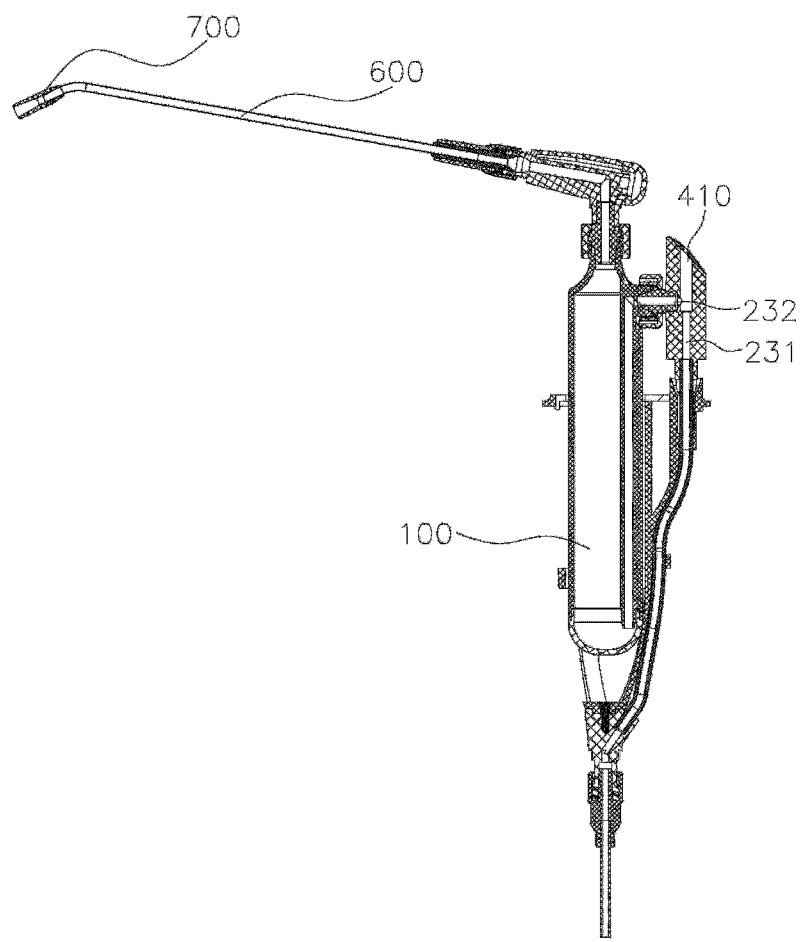
FIG. 10 is a schematic cross-sectional view of another embodiment of the apparatus in accordance with this disclosure.

FIG. 10 is a schematic cross-sectional view of another embodiment of the apparatus in accordance with this disclosure. As shown, the pressure-adjusting assembly 700 (FIG. 6) of this apparatus is assembled to one end of the connection tube 600, while another end of the connection tube 600 is connected with the device. The container 100 of the device has a containing volume of 15 cm$^3$. The pressurized fluid is firstly introduced into the pressure-in pathway 231. As the flow of the fluid is stable, the first connecting channel 410 is plugged so as to allow the pressurized fluid into the pressure-out pathway 232. After experiencing one 90° turn, the fluid would flow downward toward the pressure-route outlet 220, and would meet the medicament out of the pressure-route outlet 220. With the momentum of the fluid, the medicament at the bottom of the container 100 would be driven to the the connection tube 600. The medicament would finally be discharged out of the apparatus via the free open end of the connection tube 600 to be further applied to the bleeding wound surface by forming a medicament action area on the target tissue as shown in FIG. 9.

A middle lobe of Rat's liver is cut to make a large-scale bleeding. In the reference, a hemostatic gauze is applied directly by depression to stop the bleeding. However, bleeding still exists to all animals except for one. Among these bleeding reference, the bleeding loss is significant, and the bleeding time is comparative long. On the other hand, with the device of this disclosure to apply the hemostatic medicament to the target middle lobe, the bleeding loss at the lever is greatly reduced. In comparison with the reference, the difference between the groups is huge ($p<0.001$). The comparisons at the bleeding loss and the bleeding time for these two groups are listed in Table 1 as follow. It is shown that the comparison demonstrates significant difference ($p<0.01$) between the reference and the device of this disclosure.

TABLE 1

| Groups | Animal number (n) | Bleeding loss (g) | Bleeding time (s) |
| --- | --- | --- | --- |
| Reference | 10 | 0.64 ± 0.29 | 151.20 ± 47.73 |
| Device of Disclosure | 10 | 0.15 ± 0.07*** | 107.00 ± 31.24** |

Note:
in comparison with the reference,
"*" stands for $p < 0.05$, and
***stands for $p < 0.001$ In this test, rat's femoral artery is cut to make serious bleeding. In the reference, a hemostatic gauze is applied directly by depression to stop the bleeding. However, the bleeding loss is still significant. In the reference, 3 animals demonstrate total failure in hemostasis, and the rest show incomplete hemostasis. In all reference animals, the bleeding time is relative long. However, with the device of this disclosure to apply the hemostatic medicament, the bleeding loss is dropped ($p<0.05$), and the bleeding time is remarkably decreased. In statistics, these two groups demonstrate significant difference ($p<0.001$). In this test, no animal can reach a complete hemostasis. These results are listed in Table 2.

TABLE 2

| Groups | Animal number (n) | Bleeding loss (g) | Bleeding time (s) |
| --- | --- | --- | --- |
| Reference | 10 | 0.96 ± 0.40 | 252.9 ± 42.42 |
| Device of Disclosure | 10 | 0.59 ± 0.23* | 145.5 ± 43.02*** |

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A medicament delivery device, comprising:
a container, used for accommodating a medicament;
a pressure route, including an extending pathway, a pressure-route inlet and a pressure-route outlet, the pressure-route outlet extending toward a bottom of the container; and
a valve, including a first through hole and a valve body, the first through hole connecting spatially the pressure-route inlet and the pressure-route outlet, the valve body dividing the extending pathway into a pressure-in pathway and a pressure-out pathway.

2. The device of claim 1, wherein the device further includes a connecting port disposed at the container, the connecting port is used to connect a pressure source, and the connecting port is connected spatially with the pressure-route inlet.

3. The device of claim 1, wherein the valve body further includes a guide member for having the pressure-out pathway and the pressure-in pathway to extend toward the first through hole.

4. The device of claim 1, wherein the valve body changes at least once a flow direction of a fluid along the pressure-out pathway.

5. The device of claim 1, wherein the valve body changes at least twice a flow direction of a fluid along the pressure-out pathway.

6. The device of claim 1, wherein, after the valve body changes at least twice a flow direction of a fluid along the pressure-out pathway, the fluid in the pressure-out pathway flows toward the pressure-route outlet.

7. The device of claim 1, wherein the valve body further includes a first turning member disposed inside the pressure-out pathway to turn a flow direction of a fluid in the pressure-out pathway for a first time.

8. The device of claim 7, wherein the valve body further includes a second turning member disposed inside the pressure-out pathway to turn the flow direction of the fluid in the pressure-out pathway for a second time.

9. The device of claim 1, further including a fluid pressurized to flow along the pressure route, wherein the fluid is a gas or a liquid.

10. The device of claim 1, wherein the medicament is powdery and has more than 90% of powder particles with a grain size ≤100 μm.

11. The device of claim 1, wherein the medicament is powdery and has more than 90% of powder particles with a grain size ≤50 μm.

12. The device of claim 1, wherein the medicament is a hemostatic agent.

* * * * *